(12) United States Patent
Hung et al.

(10) Patent No.: US 7,125,967 B2
(45) Date of Patent: Oct. 24, 2006

(54) WATER-SOLUBLE CHITOSAN HAVING LOW ENDOTOXIN CONCENTRATION AND METHODS FOR MAKING AND USING THE SAME

(75) Inventors: William M Hung, Alpharetta, GA (US); Katrina L. Bergbauer, Decatur, GA (US); Kai C. Su, Alpharetta, GA (US); Guigui Wang, Cumming, GA (US); Sherry Wages, Atlanta, GA (US)

(73) Assignee: Adjuvant Pharmaceuticals, LLC, Alpharetta, GA (US)

( * ) Notice: Subject to any disclaimer, the term of this patent is extended or adjusted under 35 U.S.C. 154(b) by 93 days.

(21) Appl. No.: 10/681,560

(22) Filed: Oct. 8, 2003

(65) Prior Publication Data

US 2005/0080245 A1    Apr. 14, 2005

(51) Int. Cl.
C08B 37/08    (2006.01)
C07H 5/04    (2006.01)

(52) U.S. Cl. ....................................... 536/20; 536/55.3

(58) Field of Classification Search ................. 536/20, 536/55.3
See application file for complete search history.

(56) References Cited

U.S. PATENT DOCUMENTS

| | | | |
|---|---|---|---|
| 4,168,112 A | 9/1979 | Ellis et al. | |
| 4,259,202 A | 3/1981 | Tanaka et al. | |
| 4,826,826 A | 5/1989 | Conti | |
| 4,885,168 A | 12/1989 | Hashimoto et al. | |
| 4,909,942 A | 3/1990 | Sato et al. | |
| 4,979,959 A | 12/1990 | Guire | |
| 4,996,307 A | 2/1991 | Itoi et al. | |
| 5,057,542 A | 10/1991 | Leuba et al. | |
| 5,169,535 A | 12/1992 | Adachi et al. | |
| 5,290,813 A | 3/1994 | Clark et al. | |
| 5,409,731 A | 4/1995 | Nakagawa et al. | |
| 5,422,116 A | 6/1995 | Yen et al. | |
| 5,451,237 A | 9/1995 | Vehige | |
| 5,520,920 A | 5/1996 | Castillo et al. | |
| 5,536,155 A | 7/1996 | Futaki et al. | |
| 5,549,919 A | 8/1996 | Ueno et al. | |
| 5,589,591 A | 12/1996 | Lewis | |
| 5,658,915 A | 8/1997 | Abe et al. | |
| 5,891,913 A | 4/1999 | Sallmann et al. | |
| 6,284,749 B1 | 9/2001 | Castillo et al. | |
| 6,451,772 B1 * | 9/2002 | Bousman et al. | 514/54 |
| 6,589,999 B1 | 7/2003 | Gurny et al. | |
| 2002/0018732 A1 * | 2/2002 | Hung et al. | 422/28 |

FOREIGN PATENT DOCUMENTS

| | | | |
|---|---|---|---|
| CN | 1229071 | | 9/1999 |
| JP | 362184002 A | * | 8/1987 |
| JP | 63169975 A | | 8/1988 |
| JP | 1010970 A | | 1/1989 |
| JP | 1050014 A | | 2/1989 |
| JP | 1293314 A | | 11/1989 |
| JP | 3102313 A | | 4/1991 |
| JP | 5142502 | | 6/1993 |
| JP | 6181970 | | 7/1994 |
| JP | 7223966 A | | 8/1995 |
| JP | 7324014 | | 12/1995 |
| WO | WO 94/13774 | | 6/1994 |
| WO | WO 96/20730 | | 7/1996 |
| WO | WO 97/06782 | | 2/1997 |
| WO | WO 99/40790 | | 8/1999 |
| WO | WO 00/30609 | | 6/2000 |
| WO | WO 02/09513 A2 | | 2/2002 |

OTHER PUBLICATIONS

U.S. Appl. No. 07/986,959, Powell et al., "Compositions and Methods for Inhibiting and Reducing Lysozyme Deposition on Hydrophilic Contact Lenses," 27 pgs. (filed Dec. 9, 1992).

Brochure, "Limulus Amebocyte Lysate Endosafe KTA™, U.S. License No. 1197, Multi-Test Vial For Endotoxin (Pyrogen) Detection," *Charles River Endosafe*, 2 pgs., (Date Unknown).

Brochure, "Amino acid based surfactant, Amisoft," *Munomoto*, 6 pgs. (Date Unknown).

Brochure, "HAMPOSYL N-Acyl Sarcosinate Surfactants," *Hampshire, A Subsidiary of The Dow Chemical Company*, 30 pgs. (Date Unknown).

Bough, W. et al., "Influence of Manufacturing Variables on the Characteristics and Effectiveness of Chitosan Products. II. Coagulation of Activated Sludge Suspensions," *Biotechnology and Bioengineering*. vol. XX, No. 12, pp. 1945-1955 (Dec. 1978).

Davydova, V. et al., "Interaction of Bacterial Endotoxins with Chitosan. Effect of Endotoxin Structure, Chitosan Molecular Mass, and Ionic Strength of the Solution on the Formation of the Complex," *Biochemistry*, vol. 65, No. 9, pp. 1082-1090 (2000).

Felt, O. et al., "Topical use of chitosan in ophthalmology: tolerance assessment and evaluation of precorneal retention," *International Journal of Pharmaceutics*, vol. 180, pp. 185-193 (1999).

Felt, O. et al, "Chitosan as Tear Substitute: A Wetting Agent Endowed with Antimicrobial Efficacy," *Journal of Ocular Pharmacology And Therapeutics*, vol. 16, No. 3, pp. 261-270 (2000).

(Continued)

*Primary Examiner*—Shaojia Anna Jiang
*Assistant Examiner*—Everett White
(74) *Attorney, Agent, or Firm*—Merchant & Gould

(57) ABSTRACT

Water-soluble chitosan having a low concentration of endotoxin is disclosed. Products containing the water-soluble chitosan are also disclosed. Methods of making and using water-soluble chitosan having a low concentration of endotoxin are further disclosed.

38 Claims, No Drawings

OTHER PUBLICATIONS

Felt, O. et al., "Delivery of Antibiotics to the Eye Using a Positively Charged Polysaccharide as Vehicle," *AAPS Pharmaceutical*, http://www.pharmsci.org/scientificjournals/pharmsci/journal/01_34.html, Article 34, 9 pgs. (2001).

Hirano, S. et al., "Selective N-acylation of chitosan*," *Carbohydrate Research*, vol. 47, pp. 315-320 (1976).

Kristiansen, A. et al., "The interactions between highly de-N-acetylated chitosans and lysozyme from chicken egg white studied by $^1$H-NMR spectroscopy," *Eur. J. Biochem.*, vol. 251, pp. 335-342 (1997).

Kristiansen, A. et al., "Competitive binding of highly de-N-acetylated chitosans and N,N'-diacetylchitobiose to lysozyme from chicken egg white studied by $^1$H NMR spectroscopy," *Carbohydrate Research*, vol. 289, pp. 143-150 (1996).

Kurita, K. et al., "Studies on Chitin, 3*). Preparation of Pure Chitin, Poly(N-acetyl-D-glucosamine), from the Water-Soluble Chitin," *Makromol. Chem.*, vol. 178, pp. 2595-2602 (1977).

Kurita, K. et al., "Solubilization of a Rigid Polysaccharide: Controlled Partial N-Acetylation of Chitosan to Develop Solubility," *Carbohydrate Polymers*, vol. 16, pp. 83-92 (1991).

LeHoux, J. et al., "Some Effects of Chitosan on Liver Function in the Rat*," *Endocrinology*, vol. 132, No. 3, pp. 1078-1084 (1993).

Sannan, T. et al., "Studies on Chitin, 2*), Effect of Deacetylation on Solubility," *Makromol. Chem.*, vol. 177, pp. 3589-3600 (1976).

Wu, A. et al., "Influence of Manufacturing Variables on the Characteristics and Effectiveness of Chitosan Products. III. Coagulation of Cheese Whey Solids," *Biotechnology and Bioengineering*, vol. XX, No. 12, pp. 1957-1966 (Dec. 1978).

* cited by examiner

WATER-SOLUBLE CHITOSAN HAVING LOW ENDOTOXIN CONCENTRATION AND METHODS FOR MAKING AND USING THE SAME

FIELD OF THE INVENTION

The present invention relates to water-soluble chitosan having a low concentration of endotoxin and products containing the same. The present invention further relates to methods for making and using the water-soluble chitosan having a low concentration of endotoxin.

BACKGROUND OF THE INVENTION

Endotoxin is a lipopolysaccharide existing on the surface of the outer membrane of gram-negative bacteria and exhibits pyrogenicity. Endotoxin must be removed from pharmaceutically acceptable products.

Lipopolysaccharide endotoxin is not living bacteria and cannot be deactivated by common sterilization techniques, such as autoclaving. While gamma irradiation and dry heat sterilization techniques destroy endotoxin, these techniques may also destroy or damage many other components in a given composition. Therefore, many sterile products can contain significant levels of endotoxin unless the endotoxin is specifically removed or deactivated.

Current techniques employed in the pharmaceutical industry to remove endotoxin from biomaterials have one or more shortcomings. Size-separation techniques, such as gel permeation chromatography or ultrafiltration, provide less than acceptable results if the size of biomaterial is close to the size of endotoxin present in the biomaterial. Other techniques, such as absorption techniques, absorb endotoxin into one or more absorbents. However, if the endotoxin has a greater affinity for the biomaterial than the one or more absorbents, unacceptable separation results.

There exists a need in the art of effective methods of reducing endotoxins in chitosan and products containing chitosan.

SUMMARY OF THE INVENTION

The present invention addresses some of the difficulties and problems discussed above by the discovery of a method for making water-soluble chitosan or chitosan derivatives having a low concentration of endotoxin. In one exemplary embodiment of the present invention, the method for making water-soluble chitosan comprises contacting water-insoluble chitosan with a NaOH solution for a first period of time of greater than about one hour; partially acetylating the water-insoluble chitosan in a reaction solution containing a phase transfer agent to form partially acetylated water-soluble chitosan; dissolving the partially acetylated water-soluble chitosan in an aqueous solution containing a surfactant and having a pH of greater than 7.0; and adding a water-miscible solvent into the aqueous solution to cause precipitation of water-soluble chitosan having low endotoxin content from the aqueous solution/water-miscible solvent mixture. The exemplary method may further comprise rinsing steps, as well as, other product processing steps.

The present invention is further directed to water-soluble chitosan having a low concentration of endotoxin, and products made therefrom. One exemplary product containing water-soluble chitosan having a low concentration of endotoxin is a pharmaceutically acceptable solution, such as a preserving solution for contact lens. In one exemplary embodiment of the present invention, the water-soluble chitosan comprises partially acetylated water-soluble chitosan having a degree of N-acetylation of from about 24% to about 55%, and a degree of O-acetylation of from about 1% to about 60%, wherein the partially acetylated water-soluble chitosan comprises less than about 100 equivalent units (e.u.) of endotoxin per gram of dry water-soluble chitosan.

These and other features and advantages of the present invention will become apparent after a review of the following detailed description of the disclosed embodiments and the appended claims.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to methods for making water-soluble chitosans or chitosan derivatives having a low concentration of endotoxin, as well as, products containing the water-soluble chitosans or chitosan derivatives. The products are desirably "pharmaceutically acceptable" products. As used herein, the phrase "pharmaceutically acceptable" is used to describe a material that is not biologically or otherwise undesirable, i.e., the material may be administered to an individual without causing any undesirable biological effects or interacting in a deleterious manner with any of the other components of the pharmaceutical composition in which it is contained.

The resulting chitosans or chitosan derivatives are also "water-soluble." As used herein, the phrase "water-soluble" is used to include chitosans or derivatives thereof having a water solubility of at least about 0.2% as measured by the Water Solubility Test described below. The water-soluble chitosans or chitosan derivatives of the present invention may have water solubility of at least 0.2%, and in some cases, greater than 2%.

The Water Solubility Test comprises preparing a mixture of 0.200 g of a sample chitosan in 10 ml of deionized water, and stirring at room temperature for approximately 18 hours. The mixture is filtered through #1 qualitative filter paper. The container is washed with a small amount of deionized water. The filtrate is then placed in a weighed aluminum weighing dish and dried in a vacuum oven at around 60° C. The observed weight difference is the weight of soluble chitosan. Percent water solubility is expressed in terms of [(grams of soluble chitosan)/(grams of water)]×(100), so the maximum measurable solubility is 2.0%. As discussed above, in some cases, the water-soluble chitosans or chitosan derivatives of the present invention may have water solubility greater than 2%; however, to check the actual water solubility of these water-soluble chitosans or chitosan derivatives, more than 0.200 g of chitosan or chitosan derivative must be used in the above-described test method.

The water-soluble chitosans or chitosan derivatives are also referred to herein as being "randomly substituted partial N-, partial O-acetylated chitosans or chitosan derivatives." As used herein, the phrase "randomly substituted" is used to describe random substitution of acetyl groups on the chitosan main chain. The random substitution of acetyl groups contributes to the water solubility or hydrophilicity of the resultant chitosan polymer. As used herein, the phrase "partial N-, partial O-acetylated chitosan" or derivative thereof refers to a poly(N-, O-acetylated-D-glucosamine).

As used herein, the term "degree of deacetylation" refers to the percentage of free amino groups on the water-soluble, chitosan or chitosan derivative. The percent of N-acetylation may be calculated from the deacetylation value. The terms "percent N-acetylation" or "percent O-acetylation" also refer to the degree of —C(O)CH$_3$ substitution on either the N or O of the chitosan or chitosan derivative. It is to be understood that although greater than 50% N-acetylation is sometimes described in the art as a chitin, in the present invention, the term "chitosan" include chitosan having a percent N-acetylation of greater than 50% (i.e., includes chitins).

Examples of chitosans or chitosan derivatives include, but are not limited to, chitosan salts; water-soluble chitosan; water-soluble, randomly substituted partial N-, partial O-acetylation chitosan; chitosan oligosaccharide; carboxymethyl chitosan; and hydroxyalkyl chitosan. The hydroxyalkyl substituents of hydroxyalkyl chitosans and the carboxymethyl substituents of carboxymethyl chitosans may be attached to any of the pendant nitrogen or oxygen groups on the chitin or chitosan ring. Specific hydroxyalkyl chitosans include, but are not limited to, hydroxyethyl chitosan (also known as glycol chitosan); hydroxypropyl chitosan; dihydroxypropyl chitosan; hydroxybutyl chitosan; and dihydroxybutyl chitosan.

In a desired embodiment of the present invention, the water-soluble, randomly substituted partial N-, partial O-acetylated chitosan or derivative thereof is represented by the following formula:

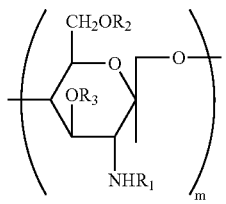

wherein R$_1$, R$_2$ and R$_3$ are each independently —H or —C(O)CH$_3$ and wherein the chitosan or derivative thereof is partially acetylated such that R$_1$ has a degree of substitution of —C(O)CH$_3$ of from about 24 to about 55%, and R$_2$ has a degree of substitution of —C(O)CH$_3$ of from about 1 to about 60%; m is greater than 25; and wherein the partial N-, partial O-acetylated chitosan or derivative thereof is randomly substituted and is water-soluble.

The term "m" is the number of repeat units in the water-soluble, chitosan or polymer chain. In one exemplary embodiment of the present invention, m is about 100,000 or higher. The molecular weight range of the water-soluble chitosan or polymer chain herein refers to the weight average molecular weight. The weight average molecular weight of the water-soluble chitosan or polymer is typically at least about 5,000. In some embodiments of the present invention, the weight average molecular weight may be up to about 3,000,000 or higher.

The present invention is directed to methods for making any of the above-described water-soluble chitosans or chitosan derivatives having a low concentration of endotoxin. Methods for making water-soluble chitosans or chitosan derivatives having a low concentration of endotoxin are described below.

I. Methods for Making Water-Soluble Chitosan Having Low Endotoxin Concentration

The present invention is directed to methods for making water-soluble chitosan or chitosan derivatives (collectively referred to herein as "chitosan" or "chitosans"). The methods of the present invention comprise a combination of steps, wherein the method comprises at least the following steps: contacting water-insoluble chitosan with a basic solution (i.e., a solution having a pH of greater than 7.0) for a period of time; and partially acetylating the water-insoluble chitosan in a reaction solution containing a phase transfer reagent to form partially acetylated water-soluble chitosan. Typically, the water-insoluble chitosan is placed in contact with a basic solution for a period of time, wherein the period of time is greater than or equal to about one hour. Desirably, the period of time is greater than or equal to about 2 hours, more desirably, from about 2 hours to about 6 hours; however, the period of time may even be greater than 6 hours if so desired.

The basic solution used to contact the water-insoluble chitosan may be a variety of basic solutions. Suitable basic solutions include, but are not limited to, alkaline hydroxides, such as potassium hydroxide or sodium hydroxide; alkaline carbonates, such as sodium carbonate, or trisodium phosphate; and combination thereof. Desirably, the basic solution used to contact the water-insoluble chitosan comprises a NaOH solution having a molar concentration ranging from 0.25M NaOH to about 1.0M NaOH, more desirably a 1.0M NaOH solution.

The basic solution treated water-insoluble chitosan is placed in a reaction solution to partially acetylate the chitosan. Desirably, the reaction solution comprises an acetylating agent and at least one phase transfer reagent. In one desired embodiment, the reaction solution has a solution pH of less than about 6.0, more desirably, from about 1.0 to about 4.0, and even more desirably, from about 2.0 to about 3.0.

Suitable acetylating agents for use in the present invention include any known acetylating agent. Exemplary acetylating agents include, but are not limited to, acetyl halides, acetic anhydride, and combinations thereof. Desirably, the acetylating agent is acetic anhydride.

Suitable phase transfer reagents for use in the present invention include any known phase transfer reagent. Suitable phase transfer reagents include, but are not limited to, those described in "Phase-Transfer Catalysis," Starks, C., et al. Chapman & Hall, 1994, which is incorporated by reference is its entirety. Example phase transfer reagents include, but are not limited to, quaternary ammonium salts having a structure as shown in Equation I below; quaternary phosphonium salts having a structure as shown in Equation II below; crown ethers having structures as shown in Equations IIIa–IIIc below; and pyridinium salts having a structure as shown in Equation IV below:

$$[A]_w[B]_x[C]_y[D]_zN^+Q^- \quad (I)$$

$$[A]_w[B]_x[C]_y[D]_zP^+Q^- \quad (II)$$

wherein:

each of w, x, y, and z is independently an integer from 0 to 4 and w+x+y+z=4;

Q is a counter-ion selected from F$^-$, Cl$^-$, Br$^-$, I$^-$, CH$_3$COO$^-$, OH$^-$, HSO$_4^-$, NO$_3^-$, PF$_6^-$, BF$_4^-$, HCOO$^-$ and H$_2$PO$_4^-$; and A, B, C and D are each independently selected from $C_1$–$C_{18}$ alkyl, phenyl in which the phenyl ring is unsubstituted or substituted by $C_1$–$C_8$ alkyl, $C_1$–$C_8$ alkoxy, halo, hydroxy, phenoxy, nitro, carboxy, acetamido, or aryl; benzyl; and cycloalkyl have 5–6 ring member of heterocyclic ring system.

In one desired embodiment, quaternary ammonium salts (I) and quaternary phosphonium salts (II) include, but are not limited to, tetra $C_1$–$C_4$ alkyl ammonium halides, such as tetrabutylammonium bromide ("TBABr"), tetramethylammonium chloride ("TMACl"), tetrabutylammonium dihydrogen phosphate ("TBADHP"), and tetrabutyl ammonium iodide ("TBAI"); benzyl tri $C_1$–$C_4$ alkylammonium halides, such as benzyltriethylammonium chloride ("BTEACI"); and tetra $C_1$–$C_{18}$ phosphonium halides, such as tetrabutyl phosphonium bromide ("TMPBr") and hexadecyltributyl phosphonium bromide ("HDTRPBr").

In a further embodiment, the phase transfer reagent comprises at least one crown ether having a structure as shown in Equations IIIa–IIIc below:

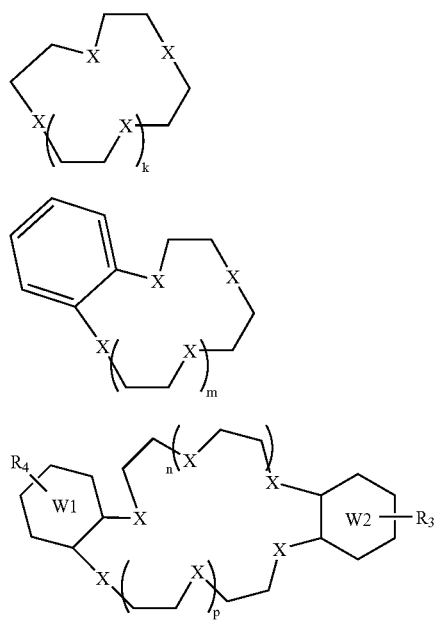

IIIa

IIIb

IIIc wherein each X independently represents O or S;

$R_3$ and $R_4$ each independently represent —H, $C_1$ to $C_4$ alkyl, or a halogen;

W1 and W2 each independently represent a cycloaliphatic ring or an aromatic ring; and k, m, n and p each independently represent integers ranging from 1 to 3.

Suitable crown ethers encompassed by Equation IIIa include, but are not limited to, 12-crown-4, 15-crown-5, 18-crown-6 and 1,4,7,10,13,16-hexathiacyclooctadecane. Suitable crown ethers encompassed by Equation IIIb include, but are not limited to, benzo-12-crown-4, benzo-15-crown-5, and benzo-18-crown-6. Suitable crown ethers encompassed by Equation IIIc include, but are not limited to, dicylohexano-18-crown-6, dicyclohexano-24-crown-8, dibenzo-18-crown-6, dibenzo-21-crown-7, dibenzo-24-crown-8, dibenzo-30-crown-10, di-tere-butyl-di-benzo-18-crown-6 and '4-bromoenzo-18-crown-6.

In yet a further embodiment, the phase transfer reagent comprises at least one pyridinium salt having a structure as shown in Equation IV below.

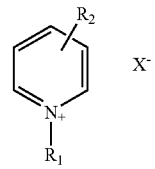

IV wherein:

$R_1$ represents $C_1$ to $C_{18}$ alkyl, benzyl, or carboxymethyl;

$R_2$ represents $C_1$ to $C_4$ alkyl, chloro, fluoro, bromo, hydroxy, $C_1$ to $C_4$ alkoxyl or alkoxylcarbonyl; and X represents a counterion of F, Cl, Br, I or p-toluene sulfonate.

Suitable pyridinium salts encompassed by Equation IV include, but are not limited to, $C_1$ to $C_{18}$ alkyl pyridinium halides, such as 1-dodecylpyridinium chloride and 1-cetylpyridinium bromide, 1-benzyl pyridinium halides, and 1-benzyl-3-hydroxypyridinium chloride.

In one desired embodiment of the present invention, the phase transfer reagent comprises a quaternary ammonium salt having a structure as shown in Equation I, more desirably, tetrabutylammonium bromide.

The solvent used in the reaction solution may be any solvent suitable for use in an acetylating reaction system. Suitable solvents include, but are not limited to, water; alcohols, such as methanol, ethanol, and isopropanol; ethers such as diethyl ether and tetrahydrofuran; polar solvents, such as dimethylormamide, dimethyl sulfoxide and N-methyl pyrrolidinone; ketones such as acetone and 2-butanone; and combinations thereof. Desirably, the solvent comprises an acidic aqueous solution (i.e., an aqueous solution having a pH of less than 7.0).

The method for making water-soluble chitosan or chitosan derivatives may further comprise one or more of the following steps:

agitating/mixing the water-insoluble chitosan in the basic solution during the basic treatment step;

rinsing the water-insoluble chitosan to remove any residual basic solution after the basic treatment step;

dissolving the partially acetylated water-soluble chitosan in an aqueous solution containing a surfactant;

adjusting a pH of the aqueous solution (containing the partially acetylated water-soluble chitosan) to a pH of about 7.0 desirably, slightly higher than 7.0, more desirably, about 7.2;

adding a water-miscible solvent into the above aqueous solution;

further adjusting the pH of the aqueous solution (containing the partially acetylated water-soluble chitosan and the water-miscible solvent) to a pH of at least 8.0 to cause precipitation of water-soluble chitosan having low endotoxin content;

separating the water-soluble chitosan having low endotoxin content from the aqueous solution; and washing the water-soluble chitosan having low endotoxin content with a water-miscible solvent.

Desirably, any rinsing step of the above-described method for making water-soluble chitosan, wherein the water-insoluble chitosan is rinsed comprises rinsing the water-insoluble chitosan with endotoxin-free water.

During the dissolving step, one or more surfactants may be added to the aqueous mixture containing dissolved partially acetylated water-soluble chitosan. Suitable surfactants include, but are not limited to, surfactants, which are block copolymers of ethylene oxide and propylene oxide and commercially available under the trade designation PLURONIC® from BASF Corporation (Mount Olive, N.J.); surfactants, which are block copolymers resulting from addition or ethylene oxide and propylene oxide to ethylene diamine and commercially available under the trade designation TETRONIC® from BASF Corporation (Mount Olive, N.J.); and polyoxyethylene sorbitan fatty acid esters commercially available under the trade designation TWEEN® from Uniqema Corporation (New Castle, Del.). Desirably, the surfactant comprises TWEEN™ 20, a polyoxyethylene sorbitan monolaurate.

Adjustments to the pH of solutions used during the above-described method for making water-soluble chitosan may be made using a variety of pH control agents. Suitable pH control agents for use in the present invention include, but are not limited to, acids, such as acetic acid, and hydrochloric acid; and bases such as those described above. Desirably, pH control agents used in the present invention to increase solution pH comprise NaOH solutions, more desirably, NaOH solutions having a NaOH molar concentration of from about 0.25M to about 1M NaOH. Desirably, pH control agents used in the present invention to decrease solution pH comprise diluted hydrochloric acid solutions.

A variety of water-miscible solvents may be used in the precipitation and washing steps of the above-described method. Suitable water-miscible solvents include, but are not limited to, isopropanol, methanol, and acetone. Desirably, the water-miscible solvent used in the present invention comprises isopropanol.

II. Water-Soluble Chitosan Having Low Endotoxin Concentration

The present invention is further directed to water-soluble chitosan having a low concentration of endotoxin, and products made therefrom. The above-described method for making water-soluble chitosan produces water-soluble chitosan having an extremely low concentration of endotoxin. The water-soluble chitosan may have a concentration of endotoxin of less than about 100 eu/gram, desirably, less than about 50 eu/gram, and more desirably, less than about 20 eu/gram of dry chitosan.

In one exemplary embodiment of the present invention, the water-soluble chitosan comprises partially acetylated water-soluble chitosan having a degree of N-acetylation of from about 24% to about 55%, and a degree of O-acetylation of from about 1% to about 60%, wherein the partially acetylated water-soluble chitosan comprises less than about 100 equivalent units (e.u.) of endotoxin per gram of dry water-soluble chitosan. Desirably, the partially acetylated water-soluble chitosan comprises less than about 50 equivalent units (e.u.) of endotoxin per gram of dry water-soluble chitosan, more desirably, less than about 20 equivalent units (e.u.) of endotoxin per gram of dry water-soluble chitosan.

III. Products Containing Water-Soluble Chitosan Having Low Endotoxin Concentration The present invention is further directed to products containing water-soluble chitosan having a low concentration of endotoxin. The water-soluble chitosan produced by the above-described method may be combined with one or more components to form a variety of products. Suitable products include, but are not limited to, solutions and compositions disclosed in U.S. patent application Ser. No. 10/045,959 filed on Oct. 19, 2001 and entitled "WATER-SOLUBLE, RANDOMLY SUBSTITUTED PARTIAL N-PARTIAL O-ACETYLATED CHITOSAN, PRESERVING COMPOSITIONS CONTAINING CHITOSAN, AND PROCESSES FOR MAKING THEREOF," the subject matter of which is incorporated herein in its entirety.

In one desired embodiment of the present invention, the product comprises a pharmaceutically acceptable solution, such as a preserving solution for contact lens, wherein the solution contains (i) water-soluble chitosan having a low concentration of endotoxin produced by the above-described method, and (ii) at least one buffer material. The preserving composition can be used in various ophthalmic products such as contact lens rinsing, lubricating, cleaning and storage solutions, artificial tear solutions and ophthalmic drugs. The preserving composition may also be used to preserve otic and nasal solutions.

Contact lens solutions in particular present a special preservative challenge because lens wearers are usually exposed to the preserving agents for many years on a daily basis. The possibility that the lens wearer can experience discomfort or develop sensitivity to the preservative is even higher than would be the case in short-term exposure. Typical contact lens solution preserving agents used in the prior art are sorbic acid, thimerosal, or DYMED™ (polyaminopropyl biguanide).

The compositions of the present invention comprise at least one chitosan or chitosan derivative having a low concentration of endotoxin, and at least one buffer solution. The compositions of the present invention may further comprise at least one biocidal adjuvant. Compositions of the present invention contain these components in amounts to be effective as pharmaceutical preserving compositions useful for preserving pharmaceutical products, including ophthalmic, nasal and otic preparations.

In one exemplary embodiment of the present invention, the composition is used as a contact lens solution preservative. In another exemplary embodiment, the composition is used as a contact lens disinfection regiment. The compositions of the present invention may be incorporated into existing contact lens solutions. When the composition of the present invention is used in a contact lens disinfection regimen, the contact lens is rinsed and rubbed with the composition, and the contact lens then soaks in the composition for a suitable period of time, such as not less than 15 minutes, more desirably for not less than 1 hour, even more desirably not less than four hours. Desirably, the soaking occurs at room temperature; however, any suitable temperature may be employed.

The compositions of the present invention containing water-soluble chitosan and chitosan derivatives having a low concentration of endotoxin have the additional advantage of being capable of performing several functions normally requiring other ingredients. For instance, in an exemplary embodiment, the chitosan or chitosan derivative may, in addition to its preserving role, act as a natural surfactant, and aid in lens cleaning by emulsifying lens proteins and lipids away from the lens surface into solution. Furthermore, chitosan, as a polymeric saccharide, may be used in an exemplary embodiment as a solution-thickening agent and lens lubricant thereby enhancing lens comfort by reducing lens drying rate. As such, the compositions of the present invention containing water-soluble chitosan and chitosan derivatives having a low concentration of endotoxin have a demulcent effect so as to enhance lens wearer comfort.

In a further embodiment of the present invention, compositions containing water-soluble chitosan and chitosan derivatives having a low concentration of endotoxin may be combined with certain buffer solutions, such as borate or phosphate buffers, to exhibit exceptional antimicrobial activity. Thus, in one embodiment of the present invention, the buffer solution may comprise a borate buffer. Suitable borate buffers include, but are not limited to, boric acid, sodium borate, potassium tetraborate, potassium metaborate, and mixtures of the same. In yet another embodiment, the buffer solution may comprise a phosphate buffer. Suitable phosphate buffers include, but are not limited to, sodium dihydrogen phosphate, disodium hydrogen phosphate, and mixtures of the same.

The compositions of the present invention may also include a biocidal adjuvant. The biocidal adjuvant may be used against, for example, bacteria, fungi and viruses. One advantage of the compositions of the present invention is the surprising synergistic preservative effect. Suitable biocidal adjuvants include, but are not limited to, disodium ethylenediaminetetracetic acid (EDTA), nitrilotriacetic acid, and ethyleneglyco-bis(β-amino-ethylether)-N,N-tetraacetic acid.

The compositions of the present invention may contain other ingredients to perform a desired function. One possible additional component may be used to allow the composition to have an osmotic pressure near that of normal lachrymal fluids. Such a function may be achieved, for instance, by a tonicity agent, such as sodium chloride, potassium chloride or glycerol.

In one desired contact lens solution of the present invention, the water-soluble chitosan having a low concentration of endotoxin acts to stabilize proteins against denaturing when compared to commercial multi-purpose contact lens solutions. This effect may be accomplished by adding at least one surfactant to the composition. The surfactant may also aid in the cleaning of the lens. Typical surfactants include, but are not limited to, surfactants, which are block copolymers of ethylene oxide and propylene oxide and commercially available under the trade designation PLURONIC® from BASF Corporation (Mount Olive, N.J.); surfactants, which are block copolymers resulting from addition or ethylene oxide and propylene oxide to ethylene diamine and commercially available under the trade designation TETRONIC® from BASF Corporation (Mount Olive, N.J.); polyoxyethylene sorbitan fatty acid esters commercially available under the trade designation TWEEN® from Uniqema Corporation (New Castle, Del.).

The contact lens solutions of the present invention may also contain viscosity agents to provide lubrication to the eye. Suitable viscosity agents include, but are not limited to, polymeric saccharides such as dextran; cellulose derivatives such as carboxymethyl cellulose and hydroxypropyl methylcellulose; polyvinyl alcohol; polyvinylpyrrolidinone; polyethylene glycol; glycerin; and combinations thereof.

The compositions of the present invention have at least a minimal preserving activity. In one embodiment, the biocidal activity of the compositions of the present invention is sufficient to meet the performance criteria of the Preservative Efficacy Test ("PET") of the USP (United States Pharmacopoeia) as modified by the FDA. As such, the compositions of the present invention reduce 0 day challenge inocula and 14 day re-challenge inocula of the bacteria *Staphylococcus aureus* (ATCC No. 6538), *Pseudomonas aeruginosa* (ATCC No. 9027) and *Escherichia coli* (ATCC No. 8739) by at least 99.99% (3 logs) within 14 days after the challenge and re-challenge dates, each. In the fungal challenge portion of the PET, the compositions of the present invention do not allow any growth of *Aspergillus niger* (ATCC No. 16404) and *Candida albicans* (ATCC No. 10231) within 14 days following a 0 day challenge and a 14 day re-challenge.

In one exemplary embodiment, the compositions of the present invention have a near neutral pH. A neutral pH is desired for compatibility with an organism, such as the human eye. Desirably, the compositions of the present invention have a pH of from about 6 to about 8, more desirably about 6.6 to about 7.8, and even more desirably about 6.8 to about 7.2. Insofar as the antimicrobial activity alone of the compositions of the present invention is concerned, the lowest pH in the above range is desired.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Determining the Concentration of Endotoxin in Water-Soluble Chitosan Solutions

The presence of endotoxins was determined in water-soluble chitosan using a Limulus Amebocyte Lysate (LAL) gel-clot assay commercially available under the trade designation ENDOSAFE® KTA (Kinetic Turbidimetric Assay) from Charles River Laboratories, Inc. (Charleston, S.C.). Sample solutions of water-soluble chitosan were prepared by dissolving a known amount of one selected batch of water-soluble chitosan sample into endotoxin-free water. The samples were agitated until completely dissolved. The pH of the solutions was about 5.

After dissolution of the water-soluble chitosan, the pH of each solution was adjusted using 1M NaOH. Each solution was then stirred for 30 to 60 minutes. The samples were then diluted serially and assayed for the presence of endotoxins. Table 1 below provides results.

TABLE 1

Sample Endotoxin Concentrations

| Sample No. | Sample pH | Average Amount of Endotoxin Detected (range of endotoxin) |
|---|---|---|
| 1 | 5.3 | 45 eu/gram (from 30–60 eu/gram) |
| 2 | 6.8 | 45 eu/gram (from 30–60 eu/gram) |
| 3 | 7.0 | 45 eu/gram (from 30–60 eu/gram) |
| 4 | 7.2 | 45 eu/gram (from 30–60 eu/gram) |
| 5 | 7.7 | 45 eu/gram (from 30–60 eu/gram) |

As shown in Table 1, adjustment of pH did not have an effect on the concentration of endotoxin detected in water-soluble chitosan solutions using the above procedure.

EXAMPLE 2

Determining the Concentration of Endotoxin in Water-Soluble Chitosan Solutions Containing a Surfactant The effect of the addition of a surfactant to the water-soluble chitosan solutions following pH adjustment was determined. Water-soluble chitosan solutions were prepared from the same batch of water-soluble chitosan sample as used in Example 1 and the pH adjusted as above in Example 1. Following pH adjustment, a surfactant, TWEEN™ 20 (polyoxyethylene sorbitan monolaurate) commercially available from Uniqema Corporation (New Castle, Del.), was added at a known concentration. The concentration of TWEEN™ 20 in the final samples was 0.008 wt %, based on a total weight of the sample. Each surfactant-containing solution was stirred for 30 to 60 minutes. Each solution was then diluted serially and assayed for the presence of endotoxins. Table 1 below provides results.

TABLE 2

Sample Endotoxin Concentrations

| Sample No. | Sample pH | Average Amount of Endotoxin Detected (range of endotoxin) |
|---|---|---|
| 1 | 5.3 | 90 eu/gram (from 60–120 eu/gram) |
| 2 | 6.8 | 180 eu/gram (from 120–240 eu/gram) |
| 3 | 7.0 | 180 eu/gram (from 120–240 eu/gram) |
| 4 | 7.2 | 180 eu/gram (from 120–240 eu/gram) |
| 5 | 7.7 | 180 eu/gram (from 120–240 eu/gram) |

As shown in Table 2, adjustment of pH along with the presence of a surfactant did have an effect on the concentration of endotoxin detected in water-soluble chitosan solutions using the above procedure. Endotoxin assay was enhanced by the adjustment of pH along with the addition of surfactant to the chitosan solution.

EXAMPLE 3

Preparation of Water-Soluble Chitosan Having Low Endotoxin Concentration

All process equipment was treated with a 1M NaOH solution and washed thoroughly with endotoxin-free water prior to use.

Basic Treatment Step A 30 g of water-insoluble chitosan having a deacetylation degree of about 84% was slurried in 1380 g of 1M NaOH solution for sixty hours. The solid was collected and washed with endotoxin-free water until the filtrate had a pH of 11 or lower.

Acetylating Step B 30 g of the above-treated water-insoluble chitosan was combined with 1000 ml of a 4 wt % acetic acid solution, 0.3 g of tetrabutylammonium bromide, and 7.5 g of acetic anhydride to partially acetylate the chitosan. 29.8 g of water-insoluble chitosan having a degree of deacetylation (DD) of about 71% was produced. The partially acetylated water-soluble chitosan was tested for endotoxin levels using the Limulus Amebocyte Lysate (LAL) gel-clot assay described in Example 1. The results are provided in Table 3 below as Example 3B.

pH/Surfactant Treatment Step C

An aqueous solution was prepared by dissolving 2.0 g of the above partially acetylated water-soluble chitosan (i.e., product from step 3B) in 70 g of endotoxin-free water and 1.0 g of 0.8 wt % TWEEN™ 20 aqueous solution. The pH was adjusted to 7.04 by adding 0.025 M NaOH solution. The solution was then diluted to a total weight of 100 g with endotoxin-free water. 25 g of isopropanol was slowly added to the solution. The pH of the solution was further adjusting to a pH of at least about 8.0 to cause precipitation of partially acetylated water-soluble chitosan from the solution by the addition of 0.025 M NaOH solution.

The precipitate was collected and washed twice with 50 g of isopropanol. The product was dried in a vacuum oven at 60° C. over night to obtain 1.5 g of solid material. The sample was tested for endotoxin levels as described above. The result are provided below in Table 3 as Example 3C.

COMPARATIVE EXAMPLE 3

Preparation of Water-Soluble Chitosan

The procedure as described in Example 3 was followed except Basic Treatment Step A was omitted. The resulting chitosan sample had a very high level of endotoxin as shown in Table 3 below compared to product of Example 3B, which was exposed to Basic Treatment Step A.

EXAMPLE 4

Preparation of Water-Soluble Chitosan Having Low Endotoxin Concentration

The procedure as described in Example 3 was followed except the final pH of the solution was raised to 9.03 in pH/Surfactant Treatment Step C. The resulting chitosan had a low level of endotoxin as shown in Table 3 below.

EXAMPLE 5

Preparation of Water-Soluble Chitosan Having Low Endotoxin Concentration

The procedure as described in Example 3 was followed except the final pH of the solution was raised to 9.61 in pH/Surfactant Treatment Step C. The resulting chitosan had a low level of endotoxin as shown in Table 3 below.

EXAMPLE 6

Preparation of Water-Soluble Chitosan Having Low Endotoxin Concentration

The procedure as described in Example 3 was followed except the final pH of the solution was raised to 10.2 in pH/Surfactant Treatment Step C. The resulting chitosan had a low level of endotoxin as shown in Table 3 below.

EXAMPLE 7

Preparation of Water-Soluble Chitosan Having Low Endotoxin Concentration

The procedure as described in Example 3 was followed except the pH/Surfactant Treatment Step C was repeated a second time. The resulting chitosan had a low level of endotoxin as shown in Table 3 below.

TABLE 3

Endotoxin Levels In Water-Soluble Chitosan

| Example No. | Endotoxin levels (eu/g) |
|---|---|
| 3B | 48–96 |
| 3C | 12–24 |
| Comparative - 3 | 6000–12000 |
| 4 | 12–24 |
| 5 | 12–24 |
| 6 | 24–48 |
| 7 | 6–12 |

EXAMPLE 8

Time Study for the Preparation of Water-Soluble Chitosan Having Low Endotoxin Concentration The procedure as described in Example 3 was followed except Basic Treatment Step A was carried out for two hours. The resulting chitosan sample had a low level of endotoxin as shown in Table 4 below.

EXAMPLE 9

Time Study for the Preparation of Water-Soluble Chitosan Having Low Endotoxin Concentration The procedure as described in Example 3 was followed except Basic Treatment Step A was carried out for six hours. The resulting chitosan sample had a low level of endotoxin as shown in Table 4 below.

TABLE 4

Endotoxin Levels in Water-Soluble Chitosan

| Example No. | Endotoxin levels (eu/g) |
|---|---|
| 8 | 48–96 |
| 9 | 12–24 |

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of making water-soluble chitosan, said method comprising the steps of:
   contacting water-insoluble chitosan with a basic solution for a first period of time;
   rinsing the water-insoluble chitosan to remove any residual basic solution;
   partially acetylating the water-insoluble chitosan in a reaction solution containing a phase transfer agent to form partially acetylated water-soluble chitosan;
   dissolving the partially acetylated water-soluble chitosan in an aqueous solution containing a surfactant;
   adjusting a pH of the aqueous solution to a pH of at least 7.0;
   adding a water-miscible solvent into the aqueous solution having a pH of at least 7.0;
   further adjusting the pH of the aqueous solution to a pH of at least 8.0 to cause precipitation of water-soluble chitosan having low endotoxin content;
   separating the water-soluble chitosan having an endotoxin content of less than about 100 equivalent units per gram of dry water soluble chitosan from the aqueous solution; and
   washing the water-soluble chitosan having low endotoxin content with the water-miscible solvent.

2. The method of claim 1, wherein the basic solution comprises a 1M NaOH solution.

3. The method of claim 1, wherein the first period of time ranges from about 1 hour to about 6 hours.

4. The method of claim 3, wherein the first period of time ranges from about 2 hour to about 6 hours.

5. The method of claim 1, wherein the aqueous solution having a pH of at least 7.0 comprises an aqueous solution having a pH of about 7.2.

6. The method of claim 1, wherein the rinsing step comprises rinsing the water-insoluble chitosan with endotoxin-free water.

7. The method of claim 1, wherein the reaction solution contains an acetylating agent selected from the group consisting of acetyl halides, acetic anhydride, and combinations thereof.

8. The method of claim 7, wherein the acetylating agent comprises acetic anhydride.

9. The method of claim 1, wherein the phase transfer agent comprises a quaternary ammonium salt, a quaternary phosphonium salt, a crown ether, or a pyridinium salt.

10. The method of claim 1, wherein the phase transfer agent comprises a quaternary ammonium salt having a structure as shown in Equation I below:

$$[A]_w[B]_x[C]_y[D]_z N^+ Q^- \qquad (I)$$

wherein:
each of w, x, y, and z is independently an integer from 0 to 4 and w+x+y+z=4;
Q is a counter-ion selected from $F^-$, $Cl^-$, $Br^-$, $I^-$, $CH_3COO^-$, $OH^-$, $HSO_4^-$, $NO_3^-$, $PF_6^-$, $BF_4^-$, $HCOO^-$ and $H_2PO_4^-$; and
A, B, C and D are each independently selected from $C_1$–$C_{18}$ alkyl; phenyl in which the phenyl ring is unsubstituted or substituted by $C_1$–$C_8$ alkyl, $C_1$–$C_8$ alkoxy, halo, hydroxy, phenoxy, nitro, carboxy, acetamido, or aryl; benzyl; and cycloalkyl have 5–6 ring member of heterocyclic ring system.

11. The method of claim 10, wherein the quaternary ammonium salt comprises tetrabutylammonium bromide.

12. The method of claim 1, wherein the phase transfer agent comprises a quaternary phosphonium salts having a structure as shown in Equation II below:

$$[A]_w[B]_x[C]_y[D]_z P^+ Q^- \qquad (II)$$

wherein:
each of w, x, y, and z is independently an integer from 0 to 4 and w+x+y+z=4;

Q is a counter-ion selected from $F^-$, $Cl^-$, $Br^-$, $I^-$, $CH_3COO^-$, $OH^-$, $HSO_4^-$, $NO_3^-$, $PF_6^-$, $BF_4^-$, $HCOO^-$ and $H_2PO_4^-$; and A, B, C and D are each independently selected from $C_1-C_{18}$ alkyl; phenyl in which the phenyl ring is unsubstituted or substituted by $C_1-C_8$ alkyl, $C_1-C_8$ alkoxy, halo, hydroxy, phenoxy, nitro, carboxy, acetamido, or aryl; benzyl; and cycloalkyl have 5–6 ring member of heterocyclic ring system.

13. The method of claim 1, wherein the phase transfer agent comprises at least one crown ether having a structure as shown in Equations IIIa–IIIc below:

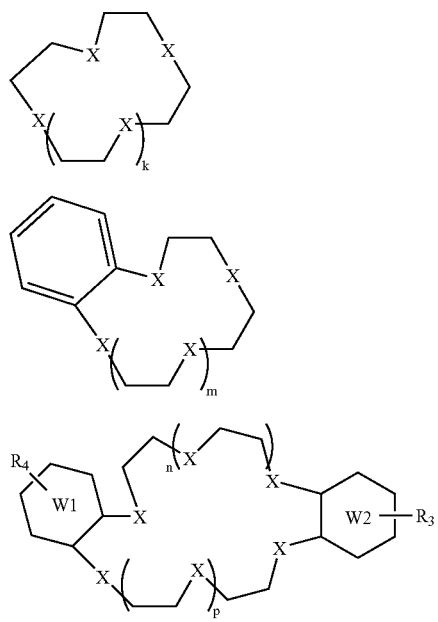

wherein each X independently represents O or S;

$R_3$ and $R_4$ each independently represent —H, $C_1$ to $C_4$ alkyl, or a halogen;

W1 and W2 each independently represent a cycloaliphatic ring or an aromatic ring; and k, m, n and p each independently represent integers ranging from 1 to 3.

14. The method of claim 1, wherein the phase transfer agent comprises at least one pyridinium salt having a structure as shown in Equation IV below:

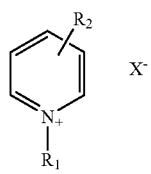

wherein:

$R_1$ represents $C_1$ to $C_{18}$ alkyl, benzyl, or carboxymethyl;

$R_2$ represents $C_1$ to $C_4$ alkyl, chloro, fluoro, bromo, hydroxy, $C_1$ to $C_4$ alkoxyl or alkoxylcarbonyl; and X represents a counterion of F, Cl, Br, I, or p-toluene sulfonate.

15. The method of claim 1, wherein the partially acetylated water-soluble chitosan has a degree of N-acetylation of from about 24% to about 55%, and a degree of O-acetylation of from about 1% to about 60%.

16. The method of claim 1, wherein the surfactant comprises polyoxyethylene sorbitan monolaurate.

17. The method of claim 1, wherein the steps of adjusting the pH of the aqueous solution comprises adding a second basic solution to the aqueous solution.

18. The method of claim 17, wherein the second basic solution comprises a 0.025 M NaOH solution.

19. The method of claim 1, wherein the aqueous solution has a pH ranging from about 7.0 to about 7.4 after the first pH adjusting step.

20. The method of claim 1, wherein the water-miscible solvent comprises isopropanol.

21. The method of claim 1, wherein the water-soluble chitosan having low endotoxin content comprises less than about 50 equivalent units (e.u.) of endotoxin per gram of dry water-soluble chitosan.

22. The method of claim 1, wherein the water-soluble chitosan has an endotoxin content of less than about 20 equivalent units (e.u.) of endotoxin per gram of dry water-soluble chitosan.

23. A method for making water-soluble chitosan, said method comprising the steps of:

contacting water-insoluble chitosan with a NaOH solution for a first period of time of greater than 1 hour;

partially acetylating the water-insoluble chitosan in a reaction solution containing a phase transfer agent to form partially acetylated water-soluble chitosan;

dissolving the partially acetylated water-soluble chitosan in an aqueous solution containing a surfactant and having a pH of from about 7.0 at about 7.4; and adding a water-miscible solvent into the aqueous solution and further adjusting the pH of the aqueous solution to a pH of at least 8.0 to cause precipitation of water-soluble chitosan having endotoxin content of less than about 100 equivalent units per gram of dry water soluble chitosan from the aqueous solution/water-miscible solvent mixture.

24. The method of claim 23, wherein the method further comprises the steps of:

after the contacting step and prior to the acetylating step, rinsing the water-insoluble chitosan to remove any residual basic solution.

25. The method of claim 24, wherein the rinsing step comprises rinsing the water-insoluble chitosan with endotoxin-free water.

26. The method of claim 23, wherein the method further comprises the steps of:

separating the water-soluble chitosan having low endotoxin content from the aqueous solution/water-miscible solvent mixture;

washing the water-soluble chitosan having low endotoxin content with the water-miscible solvent; and drying the water-soluble chitosan having low endotoxin content.

27. The method of claim 23, wherein the basic solution comprises a 1M NaOH solution.

28. The method of claim 23, wherein the first period of time ranges from about 2 hours to about 6 hours.

29. The method of claim 23, wherein the reaction solution contains an acetylating agent selected from the group consisting of acetic anhydride.

30. The method of claim 23, wherein the phase transfer agent comprises a quaternary ammonium salt, a quaternary phosphonium salt, a crown ether, or a pyridinium salt.

31. The method of claim 23, wherein the phase transfer agent comprises a quaternary ammonium salt having a structure as shown in Equation I below:

$$[A]_w[B]_x[C]_y[D]_zN+Q \quad (I)$$

wherein:

each of w, x, y, and z is independently an integer from 0 to 4 and w+x+y+z=4;

Q is a counter-ion selected from $F^-$, $Cl^-$, $Br^-$, $I^-$, $CH_3COO^-$, $OH^-$, $HSO_4^-$, $NO_3^-$, $PF_6^-$, $BF_4^-$, $HCOO^-$ and $H_2PO_4^-$; and A, B, C and D are each independently selected from $C_1$–$C_{18}$ alkyl; phenyl in which the phenyl ring is unsubstituted or substituted by $C_1$–$C_8$ alkyl, $C_1$–$C_8$ alkoxy, halo, hydroxy, phenoxy, nitro, carboxy, acetamido, or aryl; benzyl; and cycloalkyl have 5–6 ring member of heterocyclic ring system.

32. The method of claim 23, wherein the phase transfer agent comprises tetrabutylammonium bromide.

33. The method of claim 23, wherein the partially acetylated water-soluble chitosan has a degree of N-acetylation of from about 24% to about 55%, and a degree of O-acetylation of from about 1% to about 60%.

34. The method of claim 23, wherein the surfactant comprises polyoxyethylene sorbitan monolaurate.

35. The method of claim 23, wherein the aqueous solution has a pH ranging from about 7.0 to about 7.2 prior to adding the water-miscible solvent.

36. The method of claim 23, wherein the water-miscible solvent comprises isopropanol.

37. The method of claim 23, wherein the water-soluble chitosan has an endotoxin content of less than about 50 equivalent units (e.u.) of endotoxin per gram of dry water-soluble chitosan.

38. The method of claim 23, wherein the water-soluble chitosan has an endotoxin content of less than about 20 equivalent units (e.u.) of endotoxin per gram of dry water-soluble chitosan.

\* \* \* \* \*